(12) United States Patent
Nakamura (10) Patent No.: US 9,772,341 B2
(45) Date of Patent: Sep. 26, 2017

(54) AUTOMATIC POSITIONING APPARATUS

(75) Inventor: Mizuki Nakamura, Hachioji (JP)

(73) Assignee: Beckman Coulter, Inc., Brea, CA (US)

( * ) Notice: Subject to any disclaimer, the term of this patent is extended or adjusted under 35 U.S.C. 154(b) by 1392 days.

(21) Appl. No.: 12/361,805

(22) Filed: Jan. 29, 2009

(65) Prior Publication Data

US 2009/0191095 A1 Jul. 30, 2009

(30) Foreign Application Priority Data

Jan. 30, 2008 (JP) ................................ 2008-019663

(51) Int. Cl.
*G01N 35/10* (2006.01)
*G01N 35/02* (2006.01)
*G01N 35/04* (2006.01)

(52) U.S. Cl.
CPC ... *G01N 35/026* (2013.01); *G01N 2035/0493* (2013.01)

(58) Field of Classification Search
CPC ................... G01N 352/026; G01N 2035/0493
USPC ............ 422/63, 65, 67, 68.1, 105, 119, 300; 436/47, 50, 55
See application file for complete search history.

(56) References Cited

U.S. PATENT DOCUMENTS

| | | | | |
|---|---|---|---|---|
| 5,209,903 A | * | 5/1993 | Kanamori et al. | 422/65 |
| 5,985,215 A | * | 11/1999 | Sakazume et al. | 422/67 |
| 6,261,521 B1 | * | 7/2001 | Mimura | G01N 35/04 422/63 |
| 2002/0134923 A1 | * | 9/2002 | Watari | G01B 11/028 250/221 |
| 2004/0005245 A1 | * | 1/2004 | Watson | B65G 47/1471 422/65 |
| 2004/0134750 A1 | * | 7/2004 | Luoma, II | B01L 9/00 198/340 |
| 2004/0141882 A1 | * | 7/2004 | Mimura | G01N 35/00663 422/63 |
| 2004/0256571 A1 | * | 12/2004 | Muraki | G01N 21/6458 250/458.1 |

(Continued)

FOREIGN PATENT DOCUMENTS

| JP | 09-243645 | 9/1997 |
|---|---|---|
| JP | 10-115620 | 5/1998 |

(Continued)

*Primary Examiner* — Sean E Conley
*Assistant Examiner* — Benjamin R Whatley
(74) *Attorney, Agent, or Firm* — Kilpatrick Townsend & Stockton LLP (57) ABSTRACT

An automatic positioning apparatus can be used for sucking out the specimen even if the shapes of racks differ from each other is provided. The automatic positioning apparatus includes a shape-information obtaining apparatus which obtains the shape information of the rack including arrangement information of a specimen vessel, a position determining apparatus which transports racks to arrange the specimen vessel at a specimen-sucking position, and a control unit which controls the position determining apparatus to transport racks depending on shaped of the racks based on the shape information of racks. Further, the automatic positioning apparatus includes a vessel detecting apparatus which detects whether there is the specimen vessel held in the rack, and at the same time, determines a position of the specimen vessel on the transport path as an adjustment reference position.

16 Claims, 8 Drawing Sheets

(56) References Cited

U.S. PATENT DOCUMENTS

| | | | |
|---|---|---|---|
| 2005/0122521 A1* | 6/2005 | Katzlinger | G01N 21/253 356/436 |
| 2005/0163354 A1* | 7/2005 | Ziegler | G01N 15/05 382/128 |
| 2006/0093742 A1* | 5/2006 | McGlinchy et al. | 427/258 |
| 2006/0183992 A1* | 8/2006 | Kawashima | A61B 5/06 600/407 |
| 2006/0263270 A1* | 11/2006 | Rizzotte | B25J 15/0253 422/400 |
| 2007/0059209 A1* | 3/2007 | Pang | G01N 35/0095 422/72 |
| 2008/0024301 A1* | 1/2008 | Fritchie | B01L 3/545 340/572.1 |
| 2008/0050279 A1* | 2/2008 | Fujita | G01N 35/026 422/67 |
| 2008/0069730 A1* | 3/2008 | Itoh | G01N 35/026 422/65 |
| 2009/0142844 A1* | 6/2009 | Le Comte | G01N 35/00594 436/8 |

FOREIGN PATENT DOCUMENTS

| | | |
|---|---|---|
| JP | 2002-181835 | 6/2002 |
| JP | 2005-274289 | 10/2005 |
| JP | 2007-085962 | 4/2007 |

\* cited by examiner

AUTOMATIC POSITIONING APPARATUS

CROSS-REFERENCE TO RELATED APPLICATIONS

This application is based upon and claims the benefit of priority from Japanese Patent Application No. 2008-019663, filed Jan. 30, 2008, the entire contents of which are incorporated herein by reference.

BACKGROUND OF THE INVENTION

1. Field of the Invention

The present invention relates to an automatic analyzer.

2. Description of the Related Art

Conventionally, an automatic analyzer analyzes a specimen by measuring optical characteristics of a reaction liquid undergoing the reaction where the specimen and a reagent react together. A dispensing apparatus used by the automatic analyzer handles the specimen with a specimen vessel, which contains the specimen, held in a rack having a predetermined shape (e.g., see Japanese Patent Application Laid-Open No. 2007-085962).

SUMMARY OF THE INVENTION

An automatic analyzer is for analyzing a specimen in such a manner that the specimen out of a specimen vessel held in a rack which is transported along a transport path is sucked, the specimen into a reaction vessel is dispensed, and an optical characteristic of a reaction liquid obtained by reacting a reagent and the specimen in the reaction vessel is measured. The automatic analyzer includes a shape-information obtaining unit that obtains shape information of the rack; a position determining unit that transports the rack and arranges the specimen vessel at a position where the specimen is sucked out; and a control unit that controls the position determining unit to transport the rack based on the shape information of the rack.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
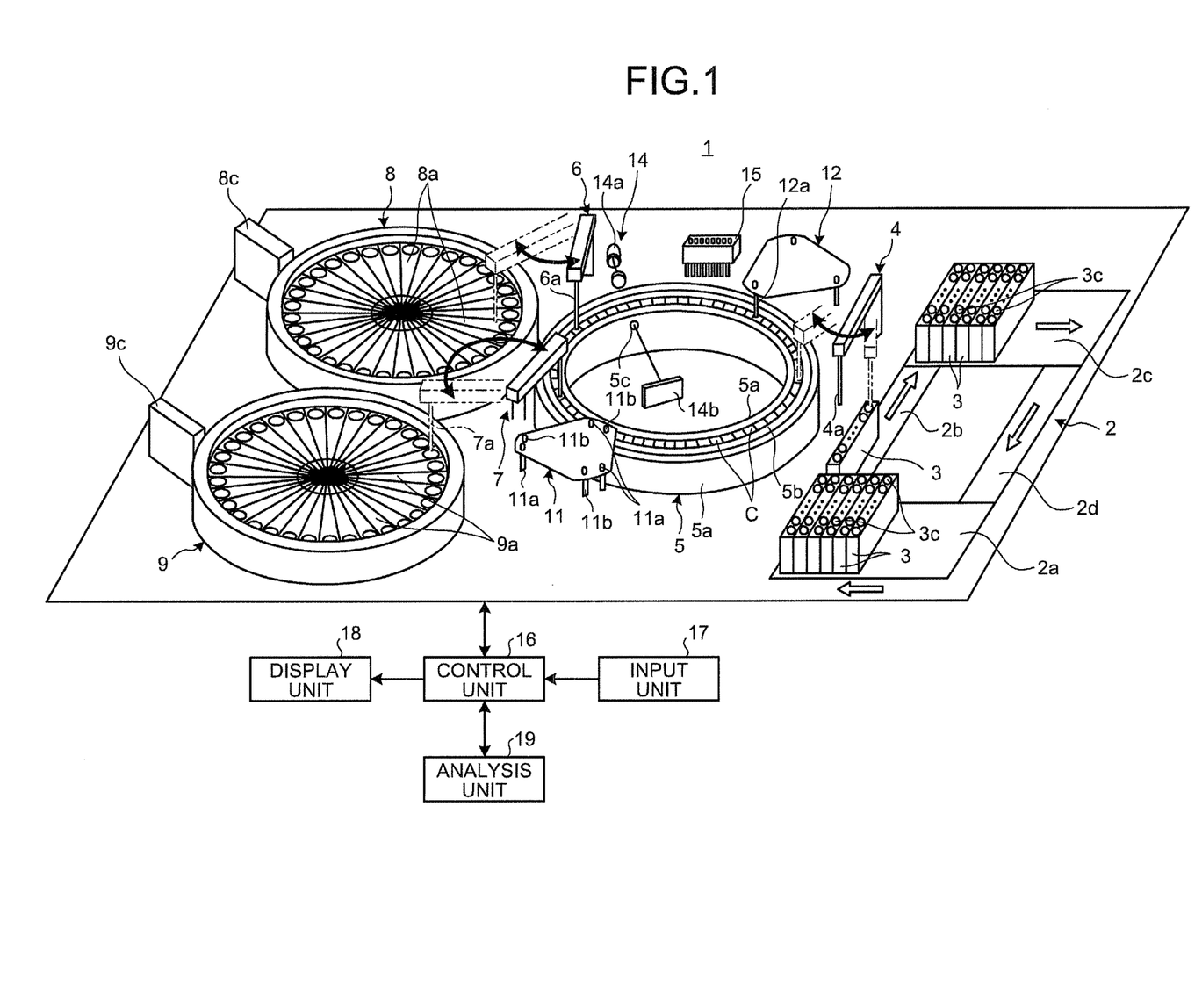
FIG. 1 shows a schematic configuration of an automatic analyzer of the present invention.
Figure 2:
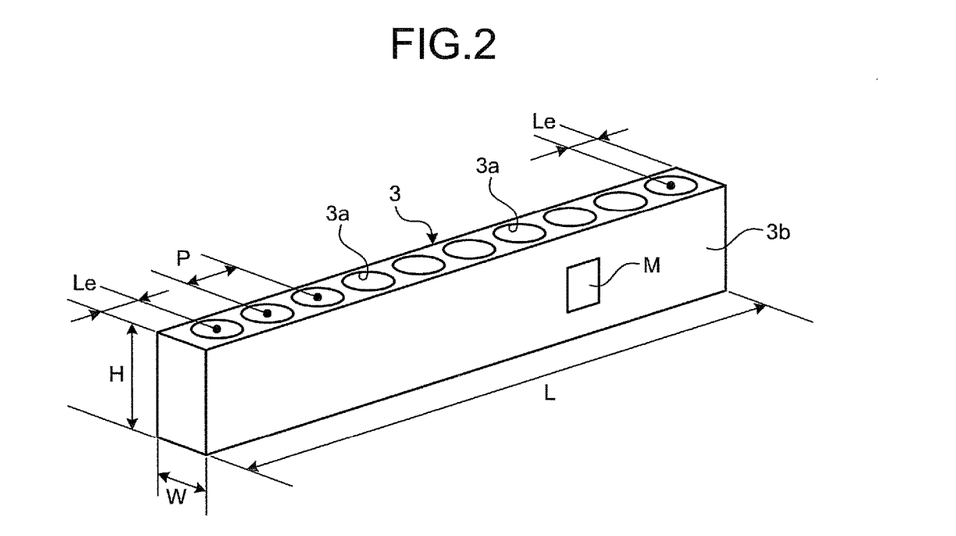
FIG. 2 is a perspective view showing an example of a rack and rack information.
Figure 3:
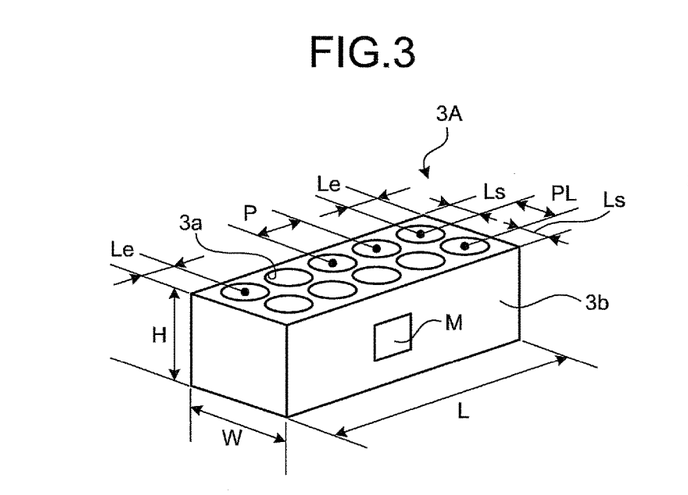
FIG. 3 is a perspective view showing another rack and rack information.
Figure 4:
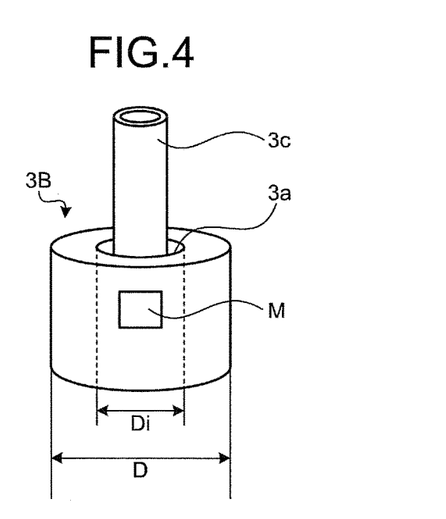
FIG. 4 is a perspective view showing still another rack and rack information.

Exemplary embodiments of an automatic analyzer according to the present invention are described in detail with reference to the accompanying drawings. FIG. 1 shows a schematic configuration of an automatic analyzer of the present invention. FIG. 2 is a perspective view showing an example of a rack and rack information. FIG. 3 is a perspective view showing another rack and rack information. FIG. 4 is a perspective view showing still another rack and rack information.

As shown in FIG. 1, an automatic analyzer 1 includes a rack transporting apparatus 2, a reaction table 5, a first-reagent refrigerator 8 and a second-reagent refrigerator 9, a first stirring apparatus 11, a second stirring apparatus 12, an optical measuring system 14, a control unit 16, and a position adjusting system 20. In the automatic analyzer 1, a specimen dispensing apparatus 4 is arranged between the rack transporting apparatus 2 and the reaction table 5, a first-reagent dispensing apparatus 6 is arranged between the reaction table 5 and the first-reagent refrigerator 8, and a second-reagent dispensing apparatus 7 is arranged between the reaction table 5 and the second-reagent refrigerator 9.

As shown in FIG. 1, the rack transporting apparatus 2 includes a transporting lane 2a, a transporting lane 2b, a retrieving lane 2c, and a re-examining lane 2d. The rack transporting apparatus 2 transports, via a caterpillar, racks having various shapes and being set at a right end of a rack-setting part. In the rack transporting apparatus 2, the position adjusting system 20 described later is arranged along the transporting lane 2b (see FIG. 5).

The transporting lane 2a transports, via the caterpillar, racks 3 (see FIG. 5) having various shapes, having a different number of concave holders 3a, and being set at the right end of the rack setting part into the transporting lane 2b. The transporting lane 2b is arranged to be orthogonal to the transporting lane 2a. The transporting lane 2b transports the racks 3 which are transported from the transporting lane 2a to the retrieving lane 2c. While the racks 3 are transported to the retrieving lane 2c along a path of the transporting lane 2b in a direction of an arrow, rack information, specimen information, and positions of specimen vessels 3c held therein are read out, and a specimen stored in each specimen vessel 3c is dispensed via a probe 4a of the specimen dispensing apparatus 4 into a cuvette C on the reaction table 5.

The retrieving lane 2c transports racks, of the racks 3 transported from the transporting lane 2b, which need to be re-examined to the re-examining lane 2d via the caterpillar. The re-examining lane 2d transports the racks 3 transported from the retrieving lane 2c to the transporting lane 2a via a belt conveyor.

As shown in FIG. 2, in the racks, plural concave holders 3a are arranged at regular pitches along a longitudinal direction, and an information recording medium M such as a bar-code label in which the rack information such as the shape and an identification number of the rack 3 is recorded and in which arrangement information of the specimen vessels 3c is recorded, is previously attached to each side wall 3b of the racks 3 along the longitudinal direction. The concave holders 3a store the specimen vessels 3c, respectively (see FIGS. 1 and 5).

The information recording medium M is attached to both side walls 3b of the rack 3 so that the rack information can be read out even if the rack 3 is set on the rack transporting apparatus 2 in the opposite direction. The rack information recorded in the information recording medium M includes, for example, a center position and a diameter of each concave holder 3a, a number of concave holders 3a, length L, width W, height H, pitch P between concave holders 3a adjacent to each other, an end-section distance Le which is distance between the end face in the front or back in the longitudinal direction and the center of the nearest concave holder 3a, and the like. On the other hand, the information recording medium (not shown) such as a bar-code label in which specimen information of a personal ID, a gender, an age, a specimen number, and the like for identifying a contained specimen is recorded, is attached to the specimen vessel 3c.

On the other hand, the racks transported by the rack transporting apparatus 2 have a different number N of the concave holders 3a, or a different size width W from those of the rack 3. Further, the racks have various shapes such as a rack 3A shown in FIG. 3, and a rack 3B shown in FIG. 4.

The rack 3A has two rows of the concave holders 3a, each row having five concave holders 3a in the longitudinal direction. Thus, the rack 3A has a same number of racks 3 (N=10). The rack information recorded in the information recording medium M include, beside the rack information described above, a row pitch PL, a side-wall distance Ls which is the distance between the center of the concave holder 3a and the side wall 3b, and the like.

The rack 3B is a cylinder-shaped rack having a single concave holder 3a for storing the specimen vessel in the center thereof. In the information recording medium, an outer diameter D and an inner diameter Di of the concave holder 3a are recorded as the rack information.

As shown in FIG. 1, the reaction table 5 includes a heat-retention member 5a and a cuvette wheel 5b. The heat-retention member 5a is arranged both inside and outside the cuvette wheel 5b along a radial direction. An opening 5c for measuring light is formed at a position opposing to the optical measuring system 14. The cuvette wheel 5b keeps the plural cuvettes C around body temperature. The cuvette wheel 5b rotates, for example, (1 circumference−1 cuvette)/4 per cycle in a clockwise direction, and thus rotates in the clockwise direction by an angle corresponding to 1 cuvette per four cycles.

Since the first-reagent refrigerator 8 and the second reagent refrigerator 9 are similarly configured, the first-reagent refrigerator 8 is described below, and a detailed description of the second-reagent refrigerator 9 is omitted. In the second-reagent refrigerator 9, the same components as the first-reagent refrigerator 8 are denoted by the corresponding numerals of those of the first-reagent refrigerator 8.

As shown in FIG. 1, in the first-reagent refrigerator 8, plural reagent bottles 8a containing the first reagents are arranged, and the predetermined reagent is dispensed into the cuvette C via a probe 6a of the first-reagent dispensing apparatus 6. The plural reagent bottles 8a are filled with the predetermined reagents which are used for analysis items, respectively. An information recording medium (not shown) such as a bar-code label and an RFID in which lot number, expiration date, and the like of the contained reagent are recorded is attached to an outer surface of the reagent bottle 8a. In the cuvette C, the specimen and the first reagent are stirred by the first stirring apparatus 11.

Further, a reagent-information reading apparatus 8c which reads out information from the information recording medium attached to each reagent bottle 8a, and outputs the information to the control unit 16 is arranged on a periphery of the first-reagent refrigerator 8. A reagent-information reading apparatus 9c reads out the information from the information recording medium attached to each reagent bottle 9a in the second-reagent refrigerator 9.

The first stirring apparatus 11 and the second stirring apparatus 12 stir the specimen and the reagent dispensed into the cuvette C with stir bars 11a, 11b, and 12a so that the specimen and the reagent are reacted together. After the dispensing and the stirring are finished, the probes 4a, 6a, and 7a of the specimen dispensing apparatus 4 and the reagent dispensing apparatuses 6 and 7 are cleaned by cleaning water supplied from a cleaning-water tank.

As shown in FIG. 1, the optical measuring system 14 includes a light source 14a and a photometry sensor 14b. The light source 14a emits analysis light for analyzing the reaction liquid in the cuvette C in which the reagent and the specimen are reacted. The photometry sensor 14b optically measures light flux which is emitted from the light source 14a and which is transmitted through the opening 5c and the reaction liquid in the cuvette C. After the reaction liquid is optically measured, the reaction liquid in the cuvette C is sucked out and disposed by a cleaning-drying unit 15. Then, the cuvette C is cleaned by detergent and cleaning water supplied from the cleaning-water tank, and dried with compressed air introduced thereinto. A new specimen is dispensed into the cuvette C again via the probe 4a of the specimen dispensing apparatus 4, and used for analyzing the specimen.

The control unit 16 is, for example, realized by a micro computer or the like having a storage function to store a result of the analysis. The control unit 16 is connected with each unit of the automatic analyzer 1. The control unit 16 controls operations of each unit of the automatic analyzer 1. When the lot number, the expiration date, or the like is out of a predetermined range according to reagent information which is read out from the information recording medium, the control unit 16 controls the automatic analyzer 1 to stop the analysis process, and may further warn an operator. Particularly, the control unit 16 controls a position determining apparatus 24 (see FIG. 7) to transport the rack 3 based on the shape information of the rack 3 obtained by a shape-information obtaining apparatus 21, to thereby arrange the specimen vessel 3c at a specimen-sucking position.

An input unit 17 is, for example, realized by a keyboard or a mouse. The input unit 17 inputs a number of specimens, analysis items, and the like to the control unit 16. A display unit 18 is realized by a display panel or the like. The display unit 18 displays a content of analysis including the analysis result, a warning including information as to whether the stirring is successfully performed, and the like.

An analysis unit 19 analyzes constituent concentration of the specimen based on absorbance (optical characteristic) of the reaction liquid of the specimen and the reagent in the cuvette C, the absorbance obtained based on a signal of light amount measured by the photometry sensor 14$b$. The analysis unit 19 stores therein the constituent concentration of the specimen.

Figure 5:
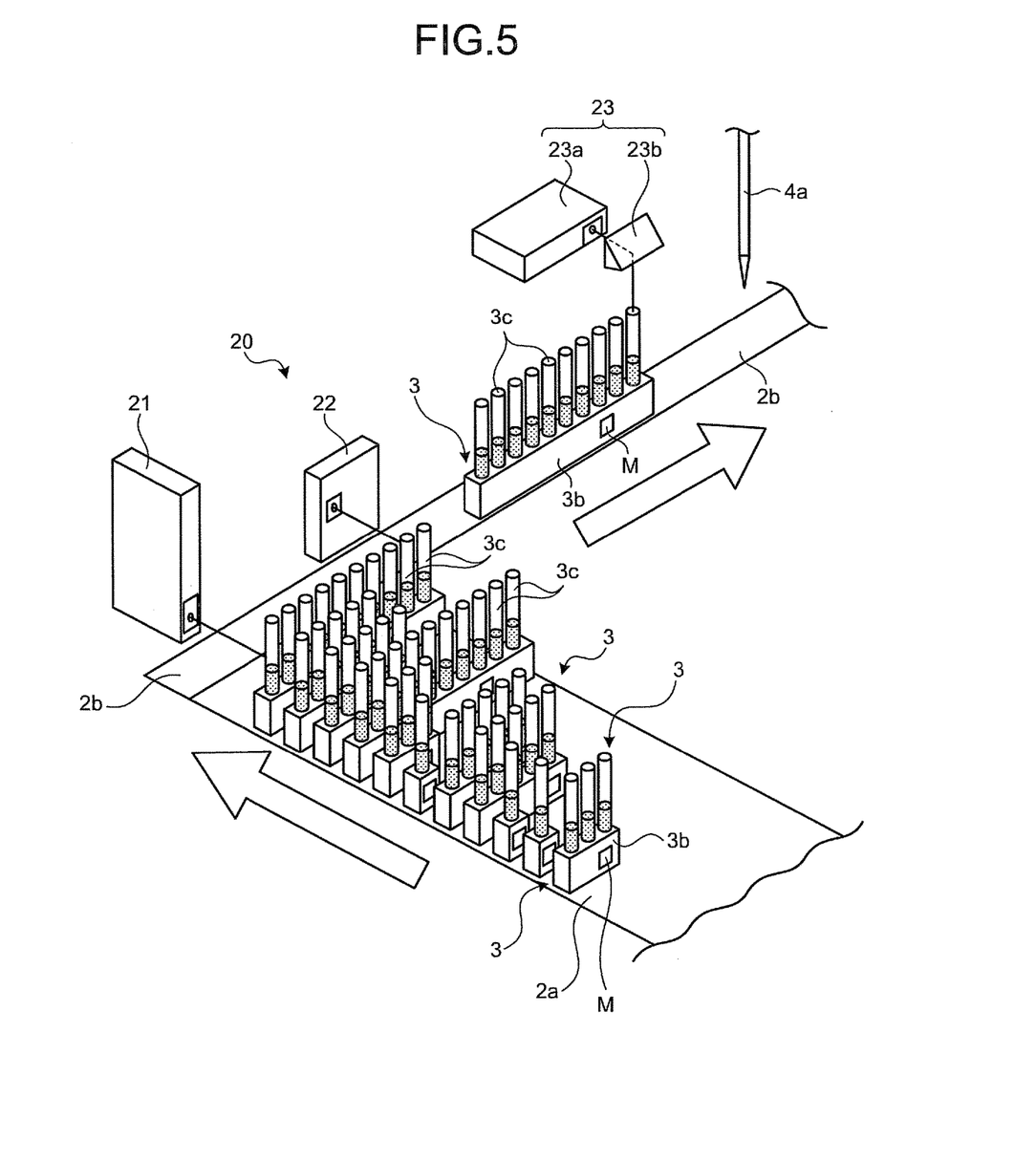
FIG. 5 is a perspective view showing an arrangement of a position adjusting system provided for the automatic analyzer.
Figure 6:
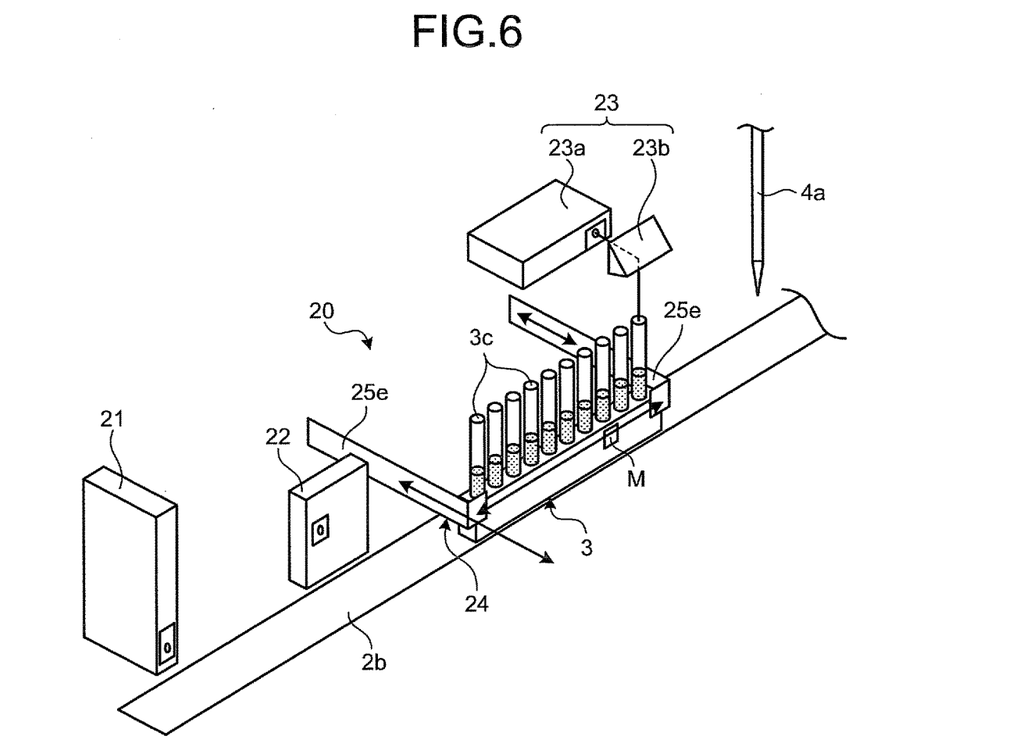
FIG. 6 is a perspective view showing an arrangement of the position adjusting system in which a carry-in lane of a rack transporting apparatus is removed from FIG. 5.
Figure 7:
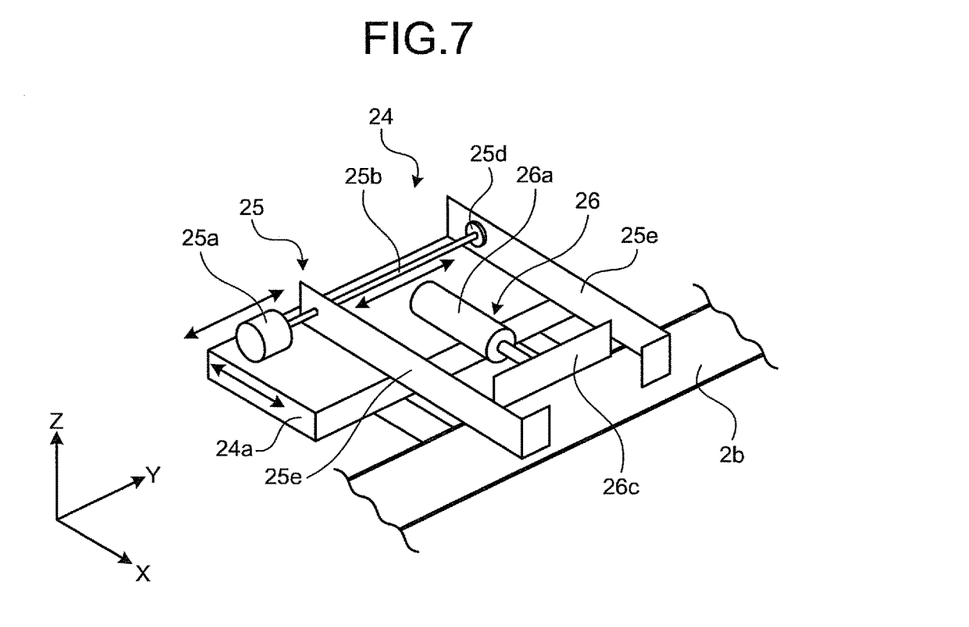
FIG. 7 shows a schematic of a position determining apparatus used by the position adjusting system.

The position adjusting system 20 includes the shape-information obtaining apparatus 21, a specimen-information reading apparatus 22, a vessel detecting apparatus 23, and the position determining apparatus 24 shown in FIGS. 5 to 7. The position adjusting system 20 moves the rack 3 based on the shape information or the shape of the rack 3 holding the specimen vessel 3$c$, and arranges the specimen vessel 3$c$ at the specimen-sucking position where the specimen is sucked out via the probe 4$a$ of the specimen dispensing apparatus 4.

The shape-information obtaining apparatus 21 obtains the shape information of the rack 3 including the arrangement information of the specimen vessel 3$c$ based on the information recording medium M attached to the rack 3 which is transported along the transporting lane 2$a$. As shown in FIG. 5, the shape-information obtaining apparatus 21 is arranged near the intersection of the transporting lane 2$a$ and the transporting lane 2$b$. The shape-information obtaining apparatus 21 outputs the read shape information of the rack 3 to the control unit 16, and also outputs the same to the control unit 16 on receiving a control signal from the control unit 16.

The vessel detecting apparatus 23 detects whether there is the specimen vessel 3$c$ held in the rack 3 based on the shape information of the rack 3 obtained by the shape-information obtaining apparatus 21. The vessel detecting apparatus 23 uses light for detecting the specimen vessel 3$c$ and determines the detected position of the specimen vessel 3$c$ as the adjustment reference position. As shown in FIG. 5, the vessel detecting apparatus 23 includes a main body 23$a$ and a prism 23$b$. The transporting lane 2$b$ stops operating under control by the control unit 16 when the rack 3 reaches the adjustment reference position where the vessel detecting apparatus 23 detects whether there is the specimen vessel 3$c$. The vessel detecting apparatus 23 detects the specimen vessel 3$c$ and determines the detected position of the specimen vessel 3$c$ as the adjustment reference position. Further, when the position determining apparatus 24 transports the rack 3 to the specimen-sucking position based on the detected adjustment reference position, the vessel detecting apparatus 23 optically detects whether there is another specimen vessel 3$c$. The main body 23$a$ emits light flux for detecting the specimen vessel 3$c$, and the light flux is refracted at the prism 23$b$ to be emitted toward the specimen vessel 3$c$. The vessel detecting apparatus 23 has a moving unit which can move the vessel detecting apparatus 23 in a direction of the transport path of the transporting lane 2$b$ and in a direction orthogonal to the described direction (in a direction X (see FIG. 7)) so that the vessel detecting apparatus 23 can accurately detect whether there is the specimen vessel 3$c$ based on the shape information of the racks 3, 3A, and 3B, and the like which is read out by the shape-information obtaining apparatus 21. The vessel detecting apparatus 23 outputs the obtained information indicating whether there is the specimen vessel 3$c$ to the control unit 16, and also outputs the information to the control unit 16 on receiving a control signal from the control unit 16.

When there is the specimen vessel 3$c$ holding the specimen, the detection light is reflected by a surface of the specimen whereas when there is an empty vessel or no specimen vessel 3$c$, the detection light is hardly reflected. Thus, the vessel detecting apparatus 23 can detect whether there is the specimen vessel 3$c$ based on the light amount of the reflected light with reference to the position of the concave holder 3$a$ based on the shaped information of the rack 3 which is read out by the specimen-information reading apparatus 22.

A Y-direction position on a horizontal surface of the detection light emitted toward the specimen vessel 3$c$ from the prism 23$b$ of the vessel detecting apparatus 23, and an X-direction position of the detection light obtained from a moving speed of the vessel detecting apparatus 23 moving with the above-described moving unit are previously input into the control unit 16. Thus, the control unit 16 determines the position of the detection light, i.e., the position of the detected specimen vessel 3$c$ as the adjustment reference position. The control unit 16 calculates the adjustment amount of two-dimensional directions (X-direction, Y-direction) for moving the specimen vessel 3$c$ toward the specimen-sucking position based on the two-dimensional positions on the horizontal surface of the plural concave holders 3$a$ which are determined from the information indicating whether there is the specimen vessel 3$c$ detected by the vessel detecting apparatus 23 and from the shape information of the rack 3 read out by the specimen-information reading apparatus 22. Then, the control unit 16 controls the position determining apparatus 24 to transport the rack 3 so that the specimen vessel 3$c$ is moved by the adjustment amount.

The position determining apparatus 24 controlled by the control unit 16 transports the rack 3 based on the shape information of the rack 3 obtained by the shape-information obtaining apparatus 21 to thereby arrange the specimen vessel 3$c$ to be at the specimen-sucking position where the specimen is sucked out by the probe 4$a$ of the specimen dispensing apparatus 4. As shown in FIG. 6, the position determining apparatus 24 is arranged between the shape-information reading apparatus 22 and the vessel detecting apparatus 23. After the rack 3 passes the position of the specimen-information reading apparatus 21, the position determining apparatus 24 starts operating, grips the rack 3, and arranges the rack 3 by transport.

As shown in FIG. 7, the position determining apparatus 24 has a gripping apparatus 25 and a pressurizing apparatus 26 arranged on an X-Y stage 24$a$. The gripping apparatus 25 grips the rack 3 on the transporting lane 2$b$ from the both longitudinal directions. The pressurizing apparatus 26 pressurizes the rack 3 from width-directions so that the rack 3 is gripped between a pair of chuck arms 25$e$ of the gripping apparatus 25. The X-Y stage 24$a$ moves in the Y-direction parallel to the transporting lane 2$b$ and in the X-direction orthogonal to the transporting lane 2$b$ on the horizontal surface. FIG. 7 shows the X and Y directions and a Z-direction orthogonal to the X-direction and Y-direction with arrows.

Figure 8:
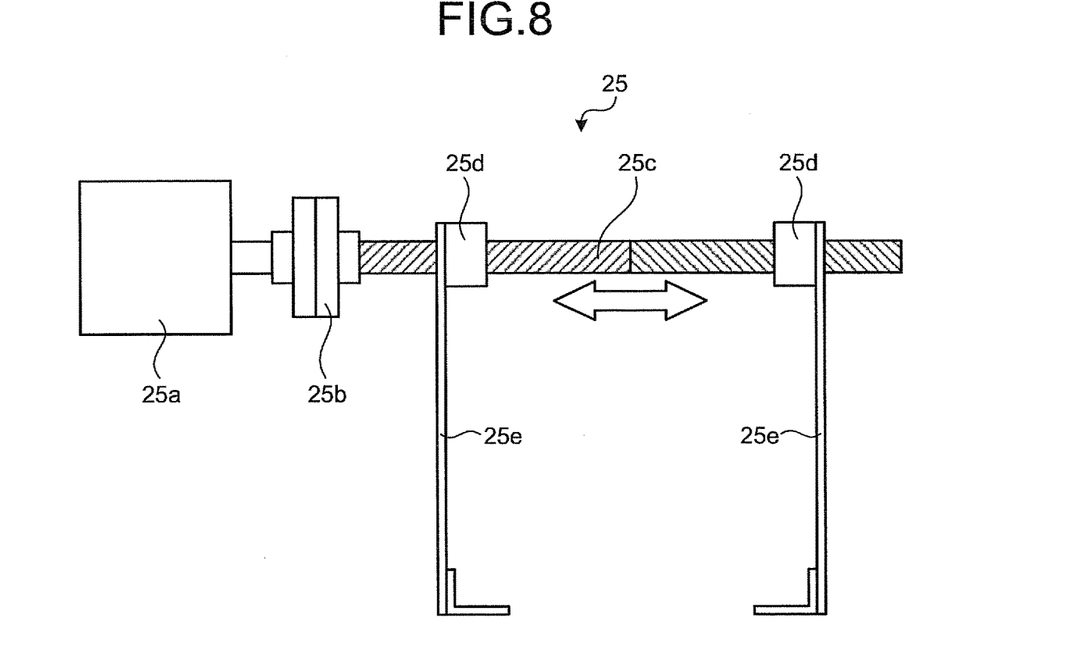
FIG. 8 is a plane view showing a specific configuration of a gripping apparatus of the position determining apparatus shown in FIG. 7.

As shown in FIGS. 7 and 8, the gripping apparatus 25 includes a driving motor 25$a$, a ball screw 25$c$, and a pair of chuck arms 25$e$. The ball screw 25$c$ is formed as a tipping end is a right screw, a proximal end where the driving motor 25$a$ is arranged is a left screw. The ball screw 25$c$ connected with the driving motor 25$a$ via a flange 25$b$. The pair of chuck arms 25$e$ is, via a nut 25$d$, attached to the right screw of the ball screw 25$c$, and to the left screw of the ball screw 25$c$, respectively. The pair of chuck arms 25$e$ folds or unfolds with the ball screw 25c screwed to the left and right, and grips the rack 3 on the transporting lane 2b from the both longitudinal directions. An antiskid material having a high coefficient of friction such as rubber may be attached to or applied to gripping parts of the chuck arms 25e so as to prevent the gripped rack 3 from falling.

Figure 9:
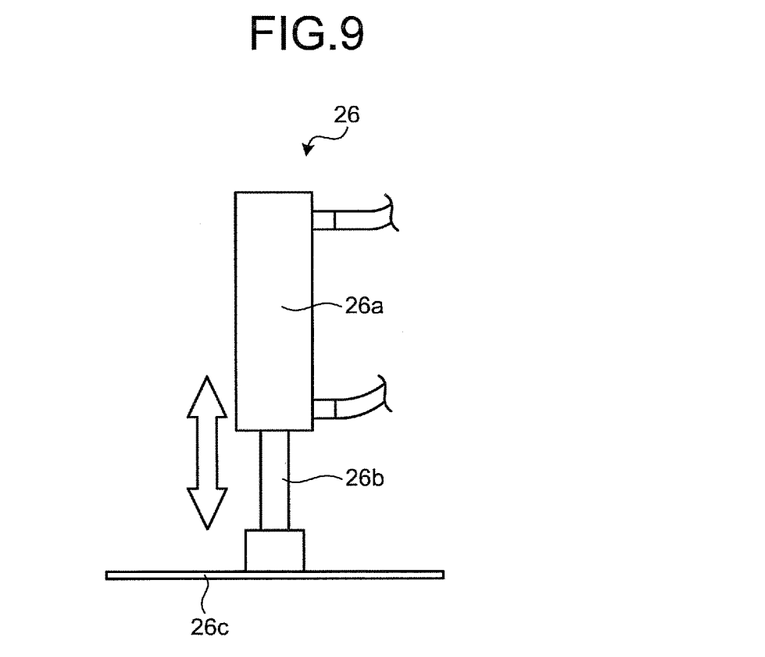
FIG. 9 is a plane view showing a specific configuration of a pressurizing apparatus of the position determining apparatus shown in FIG. 7.

As shown in FIGS. 7 and 9, the pressurizing apparatus 26 includes a fluid-pressure cylinder 26a and a pressurizing board 26c. The fluid-pressure cylinder 26a has a rod 26b which is extended or withdrawn by fluid pressure such as hydraulic pressure and air pressure, and the pressurizing board 26c is attached to a tipping end of the rod 26b. The pressurizing apparatus 26 operates in synchronization with the gripping operation of the gripping apparatus 25 for gripping the rack 3. The pressurizing apparatus 26 pressurizes the rack 3 from width directions so that the rack 3 is gripped between the chuck arms 25e.

The automatic analyzer configured as above operates under the control by the control unit 16. The first-reagent dispensing apparatus 6 sequentially dispenses the first reagent from the reagent bottle 8a into the plural cuvettes C which are circumferentially transported by the cuvette wheel 5b, and the specimen dispensing apparatus 4 sequentially dispenses the specimen stored in each specimen vessel 3c held in the rack 3.

In the cuvette C into which the reagent and the specimen are dispensed, the reagent and the specimen are stirred by the first stirring apparatus 11 and the second stirring apparatus 12 when the cuvette wheel 5b stops. When the cuvette wheel 5b starts rotating again, the cuvette C passes through the optical measuring system 14. The optical measuring system 14 measures the optical characteristic of the reagent and the reaction liquid in which the reagent and the specimen are reacted together in the cuvette C. The analysis unit 19 analyzes the constituent concentration and the like based on the light signal input from the optical measuring system 14. After the reaction liquid is measured, the cuvette C is transported to the cleaning-drying unit 15, cleaned there, and used for analyzing specimens again.

The automatic analyzer 1 includes the position adjusting system 20. The automatic analyzer 1 transports the rack 3 based on the shape information of the rack 3 and the location information of the specimen vessel 3c held in the rack 3, and arranges the specimen vessel 3c to be at the specimen-sucking position where the specimen is sucked out by the probe 4a of the specimen dispensing apparatus 4 according to the procedure described below. The control flow for the single rack 3 from obtaining the shape information of the rack 3 through sucking out the specimen to retrieving the rack 3 is described with reference to a flow chart shown in FIG. 10.

Figure 10:
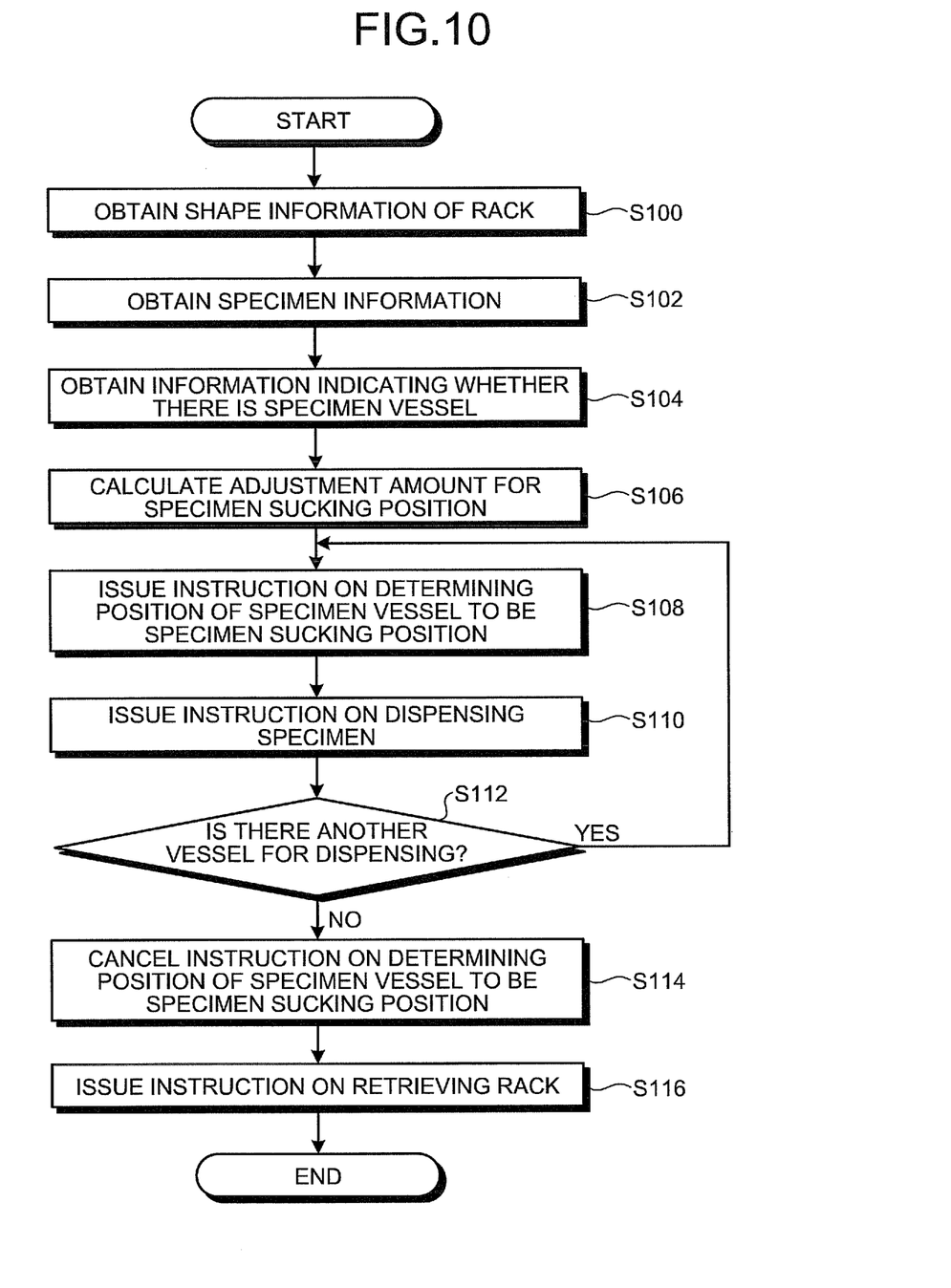
FIG. 10 is a flowchart showing a control flow with respect to a single rack from acquisition of shape information of the rack through sucking of a specimen to retrieval of the rack.

To begin with, the control unit 16 obtains the shape information of the rack 3 existing on the transporting lane 2a (Step S100). The shape information of the rack 3 is obtained via the shape-information obtaining apparatus 21. The control unit 16 obtains the specimen information (Step 102). The specimen information is obtained via the specimen-information reading apparatus 22. After the specimen information is obtained by the specimen-information reading apparatus 22, the position determining apparatus 24 grips the rack 3 in preparation for arranging the rack 3.

The control unit 16 obtains the information indicating whether there is the specimen vessel 3c from the vessel detecting apparatus 23 (Step S104). After that, the control unit 16 determines the position of the specimen vessel 3c as the adjustment reference position, and calculates the adjustment amount in two-dimensional directions, i.e., the X-direction and the Y-direction toward the specimen-sucking position from the adjustment reference position (Step S106).

The control unit 16 outputs the control signal to the position determining apparatus 24, and instructs the position determining apparatus 24 to arrange the specimen vessel 3c at the specimen-sucking position (Step S108). Based on the instruction, the position determining apparatus 24 controlled by the control unit 16 moves the rack 3 by the adjustment amount in two-dimensional directions to thereby arrange the specimen vessel 3c at the specimen-sucking position.

The control unit 16 instructs the specimen dispensing apparatus 4 to dispense the specimen (Step S110). The specimen dispensing apparatus 4 moves the probe 4a in the horizontal direction to the specimen-sucking position, lowers the probe 4a at the sucking position, and sucks out the specimen held in the specimen vessel 3c. After sucking out the specimen, the specimen dispensing apparatus 4 raises the probe 4a, moves the same in the horizontal direction, and discharges (dispenses) the specimen into the cuvette C on the reaction table 5.

The control unit 16 determines whether there is another specimen vessel 3c from which the specimen is to be sucked out (Step S112). The control unit 16 determines the above based on the shape information of the rack 3 input from the shape-information obtaining apparatus 21 and the information indicating whether there is the specimen vessel 3c obtained from the vessel detecting apparatus 23. As a result of the determining process, when there is another specimen vessel 3c (Step S112, Yes), the control unit 16 returns to Step S108 and repeats the steps following Step S108.

On the other hand, when there is no specimen vessel 3c (Step S112, No), the control unit 16 outputs the control signal to the position determining apparatus 24, and cancels the instruction to arrange the specimen vessel 3c at the specimen-sucking position (Step S114). Thus, the position determining apparatus 24 stops gripping the rack 3. After that, the control unit 16 instructs the rack transporting apparatus 2 to retrieve the rack 3 (Step S116), and terminates the control flow for the single rack 3.

In calculating the adjustment amount of the specimen vessel 3c, i.e., the adjustment amount from the adjustment reference position toward the specimen-sucking position, when the rack 3 holds plural specimen vessels 3c, the control unit 16 calculates the adjustment amount for each of the specimen vessels 3c held therein. For example, as shown in FIG. 11, when the rack 3A is held, the vessel detecting apparatus 23 first detects the specimen vessel 3c (center C1) held in the concave holder 3a positioned at a left part in front viewed along the direction of transport, and determines the X-direction, Y-direction positions (X1, Y1) on the horizontal surface of the center C1 as the adjustment reference position.

Figure 11:
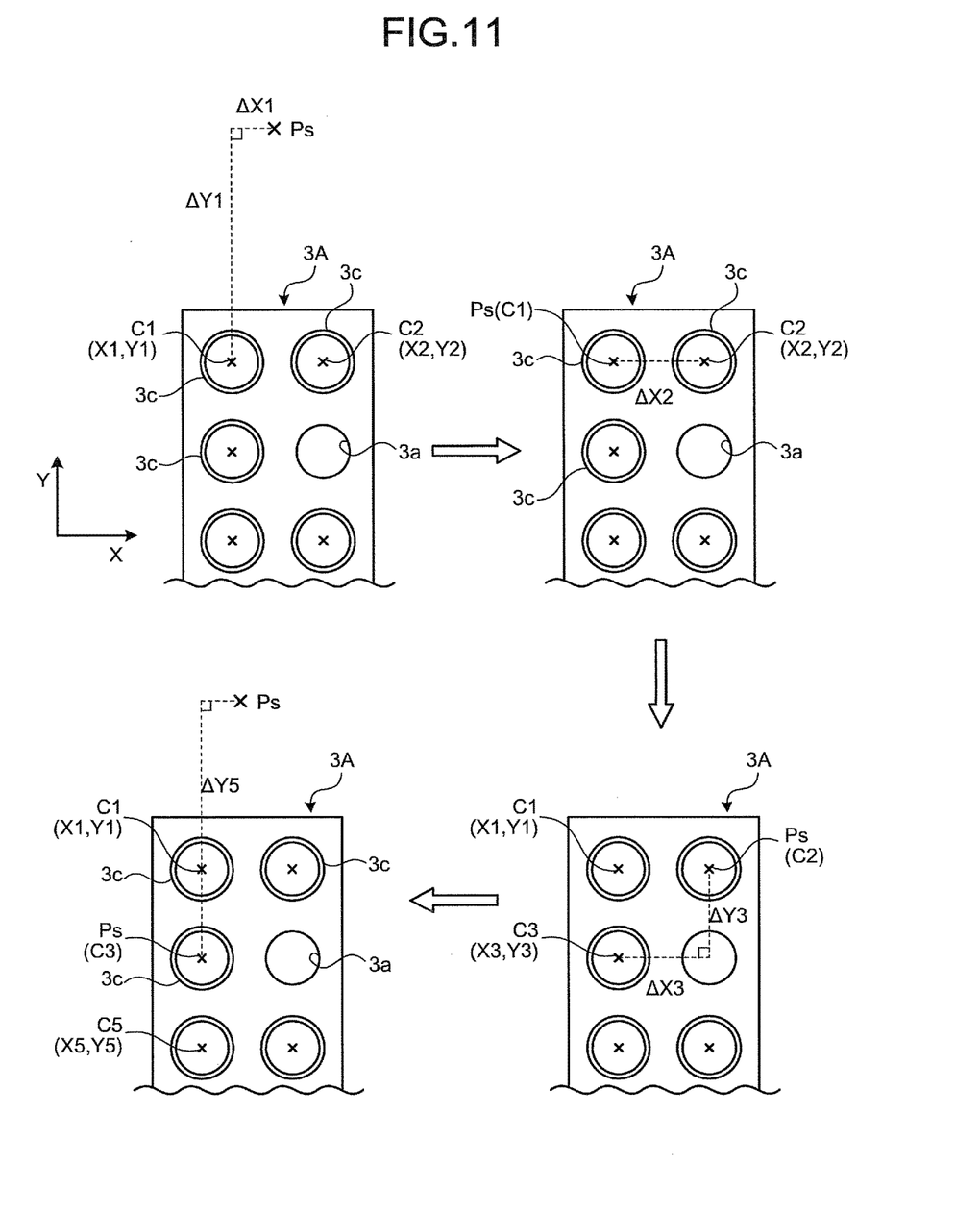
FIG. 11 illustrates calculation of an adjustment amount in two-dimensional X,Y-directions from an adjustment reference position toward a specimen-sucking position, and a process of arranging the specimen vessel at the specimen-sucking position based on the adjustment amount.

Then, as shown in FIG. 11, the control unit 16 calculates the adjustment amounts ΔX1, ΔY1 in the two-dimensional X,Y-directions from the adjustment reference position of the center C1 of the specimen vessel 3c toward the specimen-sucking position Ps (see the upper-left diagram of FIG. 11). The control unit 16 drives the position determining apparatus 24 to move the rack 3A by the adjustment amounts ΔX1, ΔY1 in the two-dimensional X,Y-directions, to thereby arrange the specimen vessel 3c (center C1) at the specimen-sucking position Ps (see the upper-right diagram in FIG. 11).

In arranging the specimen vessel 3c, the control unit 16 does not necessarily have the center C1 of the specimen vessel 3c exactly at the sucking position Ps. The control unit 16 only needs to control the position determining apparatus 24 to arrange the center of the specimen vessel 3c at a position where the specimen can be sucked out by the probe 4a of the specimen vessel apparatus 4 without the probe 4a hitting the specimen vessel 3c.

The control unit 16 determines a center C2 of the specimen vessel 3c as the adjustment reference position, and calculates the adjustment amount ΔX2 (see the upper-right diagram in FIG. 11) toward the specimen-sucking position Ps in the direction along the X axis. The adjustment amount ΔX2 is calculated based on the spatial arrangement information of the plural concave holders 3a in the two-dimensional directions on the horizontal surface which is determined from the information indicating whether there is the specimen vessel 3c in the rack 3A detected by the vessel detecting apparatus 23 and the shape-information of the rack 3, or from the shape of the rack 3. The control unit 16 drives the position determining apparatus 24 to move the rack 3A by the adjustment amount ΔX2 in the direction along the X axis to thereby arrange the specimen vessel 3c (center C2) at the specimen-sucking position Ps (see the lower-right diagram in FIG. 11).

The control unit 16 determines a center C3 of the specimen vessel 3c as the adjustment reference position, and calculates the adjustment amounts ΔX3, ΔY3 in the two-dimensional X,Y-directions toward the specimen-sucking position Ps. The control unit 16 drives the position determining apparatus 24 to move the rack 3A by the adjustment amounts ΔX3, ΔY3 in the X,Y-directions to thereby arrange the specimen vessel 3c (center 3C) at the specimen-sucking position Ps (see the lower-left diagram in FIG. 11).

After that, the control unit 16 determines a center C5 of the specimen vessel 3c as the adjustment reference position, and calculates the adjustment amount ΔY5 toward the specimen-sucking position Ps (see the lower-left diagram in FIG. 11). The control unit 16 drives the position determining apparatus 24 to move the rack 3A by the adjustment amount ΔY5 in the Y-direction to thereby arrange the specimen vessel 3c (center C5) at the specimen-sucking position Ps.

Similarly to the above, the control unit 16 determines each center of the specimen vessels 3c as the adjustment reference position, and calculates the adjustment amounts ΔXn, ΔYn (n=N) in the X, Y-directions, and drives the position determining apparatus 24 to move the rack 3 by the adjustment amounts ΔXn, ΔYn in the two-dimensional X,Y-directions to thereby arrange the specimen vessel 3c (center Cn) at the specimen-sucking position Ps.

The automatic analyzer 1 of the present invention includes the position adjusting system 20 which arranges the specimen vessel 3c at the specimen-sucking position Ps depending on the shape of the rack, whereby the automatic analyzer 1 can be used for sucking the specimen even if the shapes of the racks differ from each other.

Further, the rack transporting apparatus 2 may use a pallet conveyor instead of the caterpillar for transporting the racks.

Figure 12:
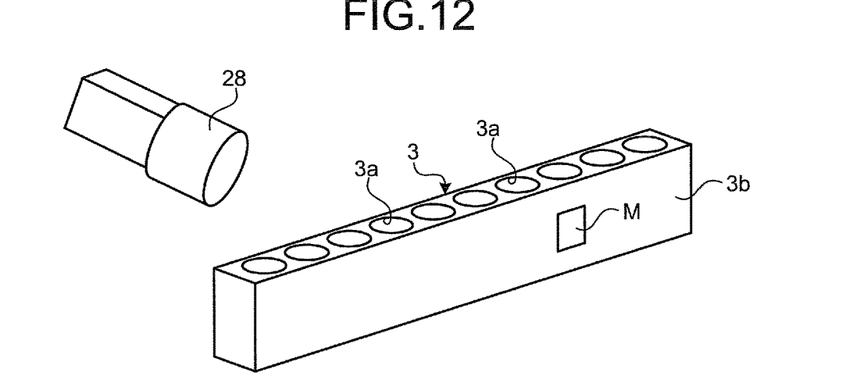
FIG. 12 is a perspective view showing a CCD camera, as a shape-information obtaining unit, which captures outer appearance of the rack.

Further, although the shape-information obtaining apparatus 21 described above reads out the shape information of the rack 3 from the information recording medium M attached to the rack 3, the shape-information obtaining apparatus 21 may, for example, use a CCD camera 28 which captures an outer appearance of the rack 3 as the shape-information obtaining apparatus as shown in FIG. 12. The CCD camera 28 outputs an image signal of the captured outer appearance of the rack 3 to the control unit 16. The control unit 16 processes the image signal of the outer appearance of the rack 3 which is input from the CCD camera 28 to thereby figure out the shape of the rack 3.

Further, although the rack 3 and the specimen vessel 3c described have the information recording medium such as the bar-code label attached thereto, the rack 3 and the specimen vessel 3c may instead have the information recording medium such as an RFID which electromagnetically stores the information attached thereto as long as the shape information of the rack and the specimen information can be obtained. In this case, the shape-information obtaining apparatus 21 and the specimen-information reading apparatus 22 use a reader/writer which electromagnetically obtains the information.

Figure 13:
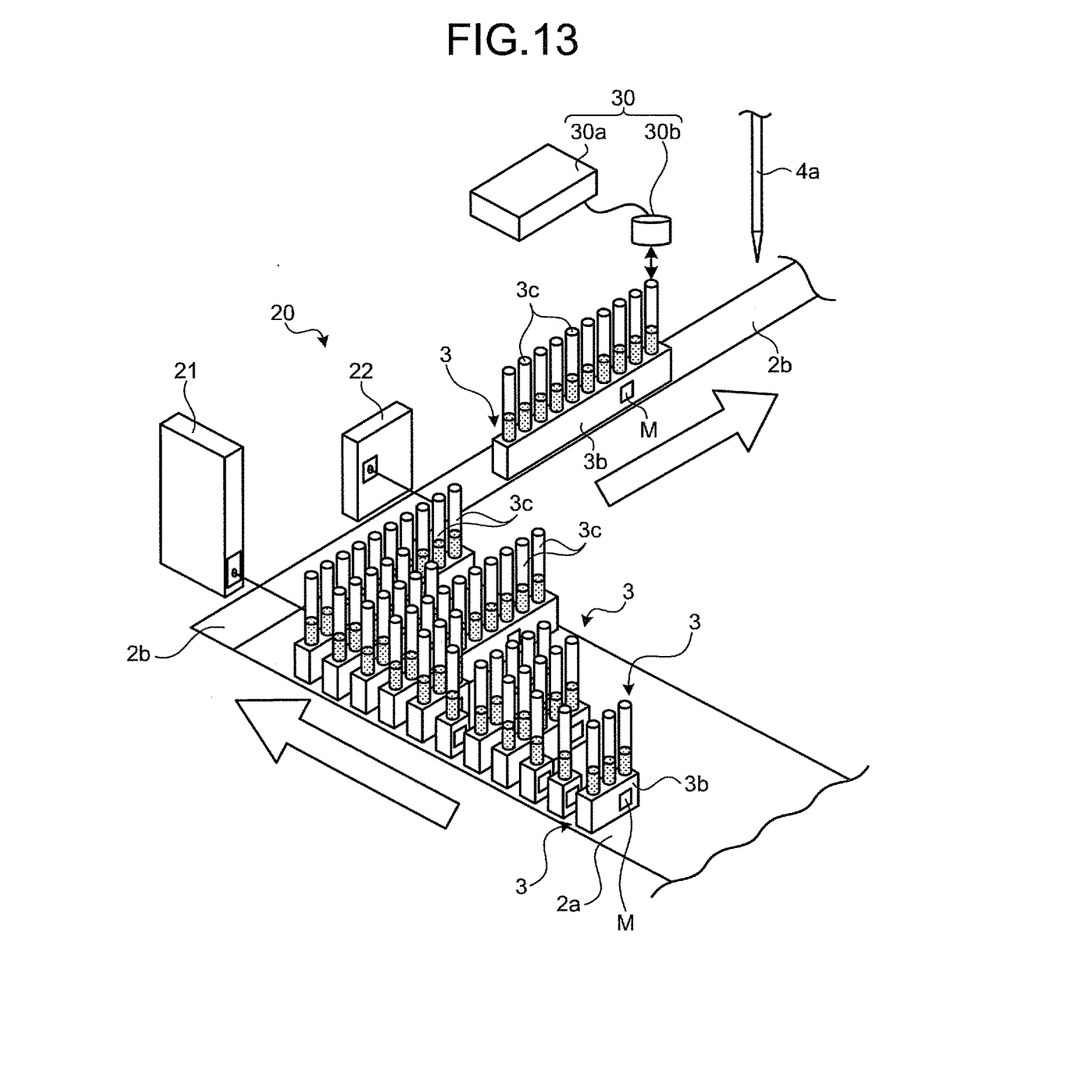
FIG. 13 is a perspective view showing an arrangement of the position adjusting system including a vessel detecting apparatus which detects whether there is the specimen vessel using ultrasonic wave.

Further, a vessel detecting apparatus 30 which detects whether there is the specimen vessel 3c using ultrasonic wave may be used as the vessel detecting unit instead of the vessel detecting apparatus 23 which detects whether there is the specimen vessel 3c using light. As shown in FIG. 13, the vessel detecting apparatus 30 includes, for example, a main body 30a and a wave-transceiving device 30b which transmits and receives the ultrasonic wave. The main body 30a outputs a control signal for detecting the specimen vessel 3c to the wave-transceiving device 30b. The wave-transceiving device 30b emits the ultrasonic wave toward the specimen vessel 3c based on the control signal input from the main body 30a, and the main body 30a determines whether there is the specimen vessel 3c based on intensity and receiving time of the ultrasonic wave reflected by the specimen vessel 3c. Similarly to the vessel detecting apparatus 23, the vessel detecting apparatus 30 has a moving unit which can move the vessel detecting apparatus 30 in the direction of transport along the transporting lane 2b and the direction orthogonal to the described direction (X-direction (see FIG. 7)) so that the vessel detecting apparatus 30 can accurately detect whether there is the specimen vessel 3c based o the shape information of the racks 3, 3A and 3B, and the like which is read out by the shape-information obtaining apparatus 21.

Further, although the position determining apparatus 24 described is configured to grip the rack from the both longitudinal directions with the pair of chuck arms 25e, the position determining apparatus 24 may grip the rack from the width directions with a pusher or the like to arrange the rack in the direction along the X axis, and transport the rack with the transporting lane to arrange the rack in the direction along the Y axis. The position determining apparatus 24 does not require the pressurizing apparatus 26 as long as the pair of chuck arms 25e of the gripping apparatus 25 can grip the rack.

Further, when plural automatic analyzers are connected together, the position adjusting system 20 of the automatic analyzer of the present invention may be arranged at the transporting unit which transports the rack to and from the adjacent automatic analyzers.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An automatic positioning apparatus comprising:
   a rack comprising a plurality of specimen vessel holders;
   a specimen vessel disposed in one of the specimen vessel holders in the plurality of specimen vessel holders and no specimen vessel is disposed in another of the specimen vessel holders in the plurality of specimen vessel holders;
   a shape-information obtaining apparatus configured to obtain shape-information of the rack from the rack, wherein the shape-information of the rack comprises information describing an external shape of the rack, external dimensions of the rack, and a spatial arrangement of the plurality of specimen vessel holders of the rack;

a position determining apparatus configured to transport the rack to a position where a specimen in the specimen vessel in the rack is sucked out by a probe;

a vessel detecting apparatus configured to detect that the specimen vessel is in the specimen vessel holder and that there is no specimen vessel in the another specimen vessel holder; and a control apparatus comprising a computer programmed to control the position determining apparatus to transport the rack in X-Y directions to the position which is based on the external shape of the rack, the external dimensions of the rack, the spatial arrangement of the plurality of specimen vessel holders of the rack obtained by the shape-information obtaining apparatus, and information from the vessel detecting apparatus that the specimen vessel holder contains the specimen vessel and that no specimen vessel is in the another specimen vessel holder.

2. The automatic positioning apparatus according to claim 1, wherein the vessel detecting apparatus is configured to set a position of a transport path of the specimen vessel as an adjustment reference position where the vessel detecting apparatus detects whether there is the specimen vessel, wherein the position determining apparatus transports the rack to the position where the specimen is sucked out by the probe based on the adjustment reference position and wherein the vessel detecting apparatus detects whether the specimen vessel is held in the rack based on the shape-information of the rack obtained by the shape-information obtaining apparatus.

3. The automatic positioning apparatus according to claim 2, wherein
the shape-information obtaining apparatus reads out the shape information of the rack from an information recording medium in which the shape-information of the rack is previously recorded, the information recording medium being attached to the rack.

4. The automatic positioning apparatus according to claim 3, wherein
the vessel detecting apparatus detects whether the specimen vessel is held in the rack based on the shape-information of the rack using light or ultrasonic waves.

5. The automatic positioning apparatus according to claim 4, wherein
the position determining apparatus comprises a gripping apparatus, configured to grip the rack, arranged on an X-Y stage configured to move the gripping apparatus in a direction along or orthogonal to a direction of the transport of the rack.

6. The automatic positioning apparatus according to claim 1 further comprising:
a second rack, the second rack having only one specimen vessel holder; and
a second specimen vessel disposed in the only one specimen vessel holder.

7. The automatic positioning apparatus according to claim 1, wherein
the rack has a box-like shape and comprises one or more specimen vessel holders in at least one row.

8. A system comprising:
a rack transporting apparatus comprising transporting lanes;

a plurality of racks with different external shapes, external dimensions or spatial arrangements of specimen vessel holders, wherein at least one rack comprises a plurality of specimen vessel holders and a specimen vessel is disposed in the one specimen vessel holder and no specimen vessel is disposed in another of the specimen vessel holders in the plurality of specimen vessel holders, wherein the rack transporting apparatus transports the plurality of racks;

a shape-information obtaining apparatus configured to obtain shape-information of each of the racks from each of the racks when the transporting lanes transport the plurality of racks, wherein the shape-information of each of the racks comprises information describing an external shape of each of the racks, external dimensions of each of the racks, and a spatial arrangement of specimen vessel holders of each of the racks;

a position determining apparatus configured to transport the plurality of racks and arrange the specimen in the specimen vessel in each rack so that the specimen is located at a position where the specimen is sucked out by a probe;

a vessel detecting apparatus configured to detect that the specimen vessel is in the specimen vessel holder and that there is no specimen vessel in the another specimen vessel holder; and a control apparatus comprising a computer and programmed to control the position determining apparatus to transport the plurality of racks in X-Y directions and arrange the specimen in the specimen vessel in each rack so that the specimen is located at the position using the external shape of the rack, the external dimensions of the rack, the spatial arrangement of specimen vessel holders of the rack obtained by the shape-information obtaining apparatus, and information from the vessel detecting apparatus that the specimen vessel holder contains the specimen vessel and that no specimen vessel is in the another specimen vessel holder.

9. The system according to claim 8, wherein the vessel detecting apparatus is configured to set a position of a transport path of the specimen vessel as an adjustment reference position where the vessel detecting apparatus detects whether there is the specimen vessel, wherein the position determining apparatus transports the plurality of racks to the positions where the specimen is sucked out by the probe based on the adjustment reference position and wherein the vessel detecting apparatus detects whether the specimen vessel is held in the rack based on the shape-information of the rack obtained by the shape-information obtaining apparatus.

10. The system according to claim 9, wherein the shape-information obtaining apparatus reads out the shape-information of the rack from an information recording medium in which the shape-information of each of the rack is previously recorded, the information recording medium being attached to each of the rack.

11. The system according to claim 10, wherein the vessel detecting apparatus detects whether the specimen vessel is held in each of the rack based on the shape-information of each of the rack using light or ultrasonic waves.

12. The system according to claim 11, wherein
the position determining apparatus comprises a gripping apparatus, configured to grip the plurality of racks, arranged on an X-Y stage configured to move the gripping apparatus in a direction along or orthogonal to a direction of the transport of the plurality of racks.

13. The system according to claim 8, wherein one of the plurality of racks has only one specimen vessel holder.

14. The system according to claim 8, wherein at least one of the racks from the plurality of racks has a tubular shape and comprises only one specimen vessel holder.

15. The system according to claim 8, wherein
at least one of the racks from the plurality of racks has a box-like shape and comprises one or more specimen vessel holders in at least one row.

16. The system according to claim 8, further comprising: the probe.

\* \* \* \* \*